United States Patent [19]

Tresper et al.

[11] 3,983,146

[45] Sept. 28, 1976

[54] PROCESS FOR THE PRODUCTION OF $\alpha$, $\alpha$, $\alpha$, $\alpha'$, $\alpha'$, $\alpha'$, -HEXAKISARYL-1,3-AND-1,4-DIMETHYL BENZENES

[75] Inventors: Erhard Tresper; Dieter Freitag, both of Krefeld; Dieter Neuray, Rumeln-Kaldenhausen, all of Germany

[73] Assignee: Bayer Aktiengesellschaft, Leverkusen, Germany

[22] Filed: May 21, 1975

[21] Appl. No.: 579,533

[30] Foreign Application Priority Data

May 24, 1974 Germany.............................. 2425193

[52] U.S. Cl. ................................................. 260/395
[51] Int. Cl.² .......................................... C09B 11/06

[58] Field of Search ..................................... 260/395

[56] References Cited
UNITED STATES PATENTS

| | | | |
|---|---|---|---|
| 3,530,152 | 9/1970 | Tokoli............................ | 260/395 X |
| 3,799,953 | 3/1974 | Freitag et al...................... | 260/395 |

*Primary Examiner*—Paul F. Shaver
*Attorney, Agent, or Firm*—Frederick H. Colen; Lawrence S. Pope; Gene Harsh

[57] ABSTRACT

The present invention relates to a process of producing $\alpha$, $\alpha$, $\alpha$, $\alpha'$, $\alpha'$, $\alpha'$-hexakisaryl-1,3- and -1,4-dimethyl benzenes by reacting $\alpha$, $\alpha$, $\alpha'$, $\alpha'$-tetrakisaryl-1,3 or -1,4-bis-(chloromethyl)- or -bis-(hydroxymethyl)- benzenes with 2 to 30 times the molar quantity (based on the tetrakis benzene) of phenol or a substituted phenol.

4 Claims, No Drawings

PROCESS FOR THE PRODUCTION OF $\alpha, \alpha, \alpha, \alpha', \alpha', \alpha'$,-HEXAKISARYL-1,3-AND-1,4-DIMETHYL BENZENES

SUMMARY OF THE INVENTION

This invention relates to a process for the production of $\alpha, \alpha, \alpha, \alpha', \alpha', \alpha'$-hexakisaryl-1,3- and -1,4-dimethyl benzenes corresponding to the general formula (I)

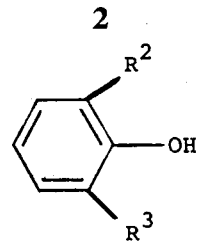

(III)

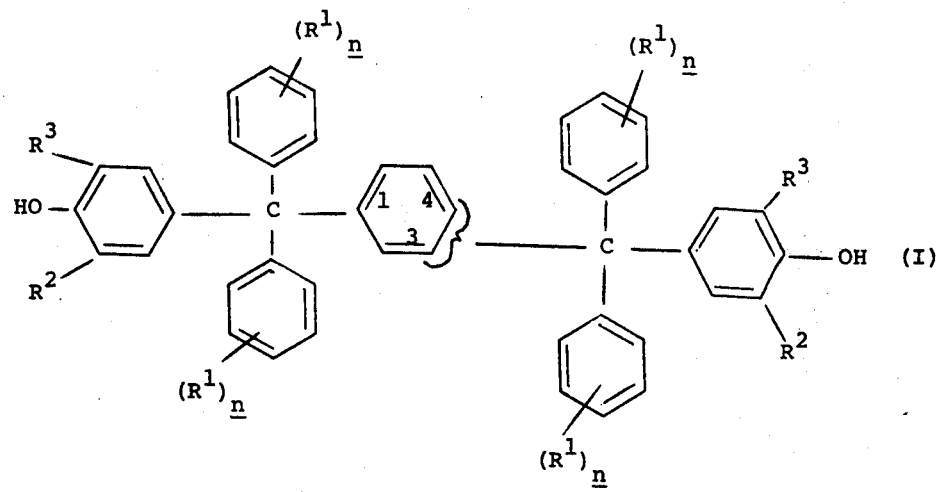

(I)

in which
R¹ represents hydrogen, $C_1$–$C_4$ alkyl or halogen, preferably H, $CH_3$, F, Cl or Br;
n = 1, 2 or 3; and
R² and R³ independently of one another represent hydrogen, $C_1$-$C_3$-alkyl or halogen (for example Cl or Br), preferably H, which is characterized by the fact that $\alpha, \alpha, \alpha', \alpha'$-tetrakisaryl-1,3- or -1,4-bis-(chloromethyl)- or -bis-(hydroxymethyl)-benzenes corresponding to the general formula (II)

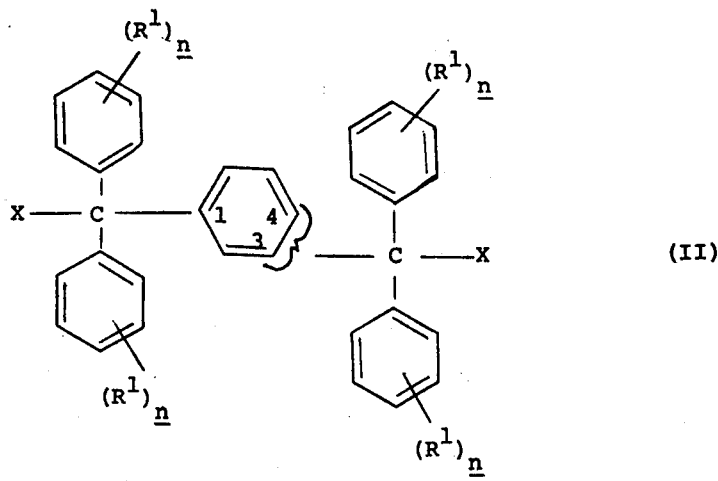

(II)

in which X represents chlorine or OH and R¹ and n are as defined for formula I,
are reacted with about 2 to 30 times the molar quantity, preferably with about 6 to 15 times the molar quantity, of a phenol corresponding to the general formula (III)

in which R² and R³ are as defined with reference to formula I,
at temperatures in the range from about 30°C to 300°C and preferably at temperatures in the range from about 60°C to 200°C.

Hitherto, it has only been possible to obtain compounds of the type corresponding to formula I from p-bis-(di-phenyl hydroxymethyl)-benzene in glacial acetic acid/sulphuric acid in accordance with Baeyer Villiger (cf. Ber. dtsch. chem. Ges. 37, pp 2001 et seq in particular page 2007 (1904), and Zeitschrift fṳ Naturforschung 13b (1958), page 825).

Compared with this prior method, which is carried out in glacial acetic acid/sulphuric acid, the process according to the invention affords a significant techn cal advance, especially since the excess phenol can readily be recovered and re-used for new reactions.

DETAILED DESCRIPTION OF THE INVENTION

The 1,3- and 1,4-bis-(chloromethyl)-benzenes or 1,3- and 1,4-bis-(hydroxymethyl)-benzenes suitable for use as starting compounds of formula II in the process according to the invention, unless already known from the literature, may be obtained as follows in accordance with German Patent Application No. P 24 25 194.3 filed on the same date:

For example a solution of a 1,3- or 1,4-isomeric $\alpha, \alpha, \alpha, \alpha', \alpha', \alpha'$-hexachlorodimethyl benzene in an aromatic solvent which is also a reactant, is added dropwise to a suspension and/or solution of a Friedel-Crafts catalyst in the corresponding aromatic solvent, followed by stirring at temperatures in the range from 30° to 80°C until the evolution of hydrogen chloride stops. The required $\alpha, \alpha, \alpha, \alpha', \alpha'$-tetrakisaryl-$\alpha,\alpha'$-dichloro- or -$\alpha, \alpha'$-dihydroxy dimethyl benzenes are then obtained, frequently in quantitative yields, depending on whether concnetrated hydrochlorid acid or water is used for working up.

The following are examples of compounds corresponding to the general formula (II) which may be obtained in this way:

$\alpha, \alpha, \alpha', \alpha'$-tetrakisphenyl-$\alpha, \alpha'$-tetrakisphenyl-$\alpha,\alpha'$-dihydroxy-p-xylene;

$\alpha, \alpha, \alpha', \alpha'$-tetrakisphenyl-$\alpha.\alpha'$-dichloro-p-xylene;

$\alpha, \alpha, \alpha', \alpha'$-tetrakisphenyl-$\alpha,\alpha'$-dihydroxy-m-xylene;

$\alpha, \alpha, \alpha', \alpha'$-tetrakisphenyl-$\alpha,\alpha'$-dichloro-m-xylene;

$\alpha, \alpha, \alpha', \alpha'$-tetrakis-(p-fluorophenyl)-$\alpha,\alpha'$-dihydroxy-p-xylene;

$\alpha, \alpha, \alpha', \alpha'$-tetrakis-(p-fluorophenyl)-$\alpha,\alpha'$-dichloro-p-xylene;

$\alpha, \alpha, \alpha', \alpha'$-tetrakis-(p-chlorophenyl)-$\alpha,\alpha'$-dihydroxy-p-xylene;

$\alpha, \alpha, \alpha', \alpha'$-tetrakis-(p-chlorophenyl)-$\alpha,\alpha'$-dihydroxy-m-xylene;

$\alpha, \alpha, \alpha', \alpha'$-tetrakis-(p-chlorophenyl)-$\alpha,\alpha'$-dichloro-p-xylene;

$\alpha, \alpha, \alpha', \alpha'$-tetrakis-(p-chlorophenyl)-$\alpha,\alpha'$-dichloro-m-xylene;

$\alpha, \alpha, \alpha', \alpha'$-tetrakis-(p-bromophenyl)-$\alpha,\alpha'$-dihydroxy-p-xylene;

$\alpha, \alpha, \alpha', \alpha'$-tetrakis-(p-bromophenyl)-$\alpha,\alpha'$-dichloro-p-xylene;

$\alpha, \alpha, \alpha', \alpha'$-tetrakis-(m,p-dichlorophenyl)-$\alpha,\alpha'$-dihydroxy-p-xylene;

$\alpha, \alpha, \alpha', \alpha'$-tetrakis-(m,p-dichlorophenyl)-$\alpha,\alpha'$-dichloro-p-xylene;

and $\alpha, \alpha, \alpha', \alpha'$tetrakis-(p-methylphenyl)-$\alpha,\alpha\alpha'$-dichloro-p-xylene.

The compounds of formula II may even be used without being previously isolated, as shown in Example 5 hereinafter. Thus after such compounds have been prepared in accordance with Patent Application No. P 24 25 194.3, they are immediately utilized in the process according to the present invention.

Other starting compounds for the process according to the invention and reactants for the aforementioned tetrakisaryldichloro- and -dihydroxy-dimethyl benzenes are the phenols of general formula III previously defined which are known from the literature. Examples of these compounds include phenol, ortho-substituted methyl, ethyl, propyl, isopropyl, chlorophenols or bromophenols and the corresponding o, o'-disubstituted phenols.

The hydrogen chloride evolved in cases where bis-chloro-methyl benzenes of formula II are used escapes from the reaction mixture in gaseous form. Residues can be removed by introducing nitrogen or by applying a vacuum.

The water of reaction formed where the bis-hydroxymethyl benzenes of formula II are used can readily be separated off, for example by azeotropic distillation following the addition of an inert entraining agent, such as toluene or xylene, which can be recycled. The water of reaction formed can also be removed from the reaction mixture by distillation in the form of a phenol/water mixture. In this case, the phenol of formula III used in excess as reactant is used as entraining agent.

It is also possible, by introducing hydrogen chloride gas before and/or during the production of the compounds of formula I from the dihydroxy methyl benzenes of formula II, to use the corresponding dichloromethyl benzenes of formula II in situ. In this case, it is possible by increasing the reaction temperature for the water of reaction formed to be removed from the reaction mixture by distillation in the form of concentrated hydrochloric acid during preparation of the compounds of formula I.

There is no need to use a diluent or solvent in the process according to the invention. Where phenol is present in excess, the temperature of the reaction mixture is kept at such a high level during and after the reaction that a stirrable suspension of the reaction product in the excess phenol is obtained. Where the reaction according to the invention is carried out without an excess of phenol, the reaction temperature has to be permenently kept at such a high level that the reaction mixture remains liquid and, hence, stirrable.

In the case of the $\alpha, \alpha'$-dichlorodimethyl benzenes of formula II, the reaction is complete when the evolution of hydrogen chloride stops. Another sign that the reaction is complete is the fact that the reaction mixture distinctly lightens. In the case of $\alpha, \alpha'$-dihydroxydimethyl benzenes of formula II, the progress of the reaction can be monitored through the formation of water. In every case, it has proved to be advantageous to leave the reaction mixture reacting for a while at the temperatures reached towards the end of the reaction.

On completion of the reaction, the reaction mixture is diluted with an organic solvent, for example methylene chloride, ethanol, toluene or cyclohexanone, excess phenol being dissolved while the $\alpha, \alpha, \alpha', \alpha'$-tetrakisaryl-$\alpha,\alpha'$-bis-(hydroxy-phenyl)dimethyl benzene formed remains behind undissolved and, hence, may be separated off.

In some cases, it has proved to be advantageous initially to separate off some of the phenol used in excess by distillation, optionally in vacuo, and only then to proceed on the lines described above.

The reaction product is purified by conventional methods, for example by recrystallization from cyclohexanone. More elaborate purification techniques, such as zone melting or chromatographic techniques, may of course also be used.

The reaction time is governed by the type and quantity of the reactants. It can range from one to several hours, although in general the reaction is over after 2 to 6 hours.

The reaction temperature is also governed by the reactivity of the starting compounds. It can be in the range from 30° to 300°C, although the reaction is preferably carried out at temperatures in the range of from 60° to 200°C.

In general, the process according to the invention can be carried out for example by dissolving or suspending the α, α, α', α'-tetrakisaryl-α,α'-dichloro-or -dihydroxy dimethyl benzenes in several times the molar quantity, for example 10 times the molar quantity of a phenol, approximately 10°C above the melting temperature of the phenol used. In many cases, the reaction then begins spontaneously, and all that is necessary in order to obtain a better yield is an increase in temperature adapted to the evolution of hydrogen chloride or to the formation of water.

The process according to the invention can be carried out under normal pressure, under elevated pressure and even under reduced pressure.

The process according to the invention can be carried out both in batches, for example in a vessel or autoclave, and also continuously, for example in a tube. The various possibilities available for carrying out the process according to the invention on a commercial scale, and the apparatus used for this purpose, are known from the prior art.

The following compounds for example may be produced by the process according to the invention:

α, α, α', α'-tetraphenyl-α,α'-bis-(4-hydroxyphenyl)-1,4-dimethyl benzene;
α, α, α', α'-tetraphenyl-α,α'-bis-(4-hydroxyphenyl)-1,3-dimethyl benzene;
α, α, α', α'-tetrakis-(4-fluorophenyl)-α,α'-bis-(4-hydroxyphenyl)-1,4-dimethyl benzene;
α, α, α', α'-tetrakis-(4-chlorophenyl)-α,α'-bis-(4-hydroxyphenyl)-1,4-dimethyl benzene;
α, α, α', α'-tetrakis-(3,4-dichlorophenyl)-α,α'-bis-(4-hydroxyphenyl)-1,4-dimethyl benzene;
α, α, α', α'-tetraphenyl-α,α'-bis-(4-hydroxy-3,5-dimethylphenyl)-1,4-dimethyl benzene;
α, α, α', α'-tetraphenyl α,α'-bis-(4-hydroxy-3-chloro-phenyl)-1.4-dimethyl-benzene; and α. α. α'. α'-tetrakis-(p-methylphenyl)-α.α'-bis-(4-hydroxyphenyl)-1.4-dimethyl-benzene.

The process according to the invention may of course also be modified by using acid, especially weakly acid, catalysts. The use of catalysts of this kind in condensation reactions with phenols is known in principle. Catalysts suitable in the present case are Lewis acids, inorganic proton acids such as hydrochloric acid, sulphuric acid, phosphoric acid, organic proton acids for example, the carboxylic acids, acetic acid, propionic acid, benzoic acid, adipic acid and phthalic acid, derivatives of carboxylic acids, such as salts with metals, with ammonia and amines which act like acids under the reaction conditions, for example calcium benzoate, zinc acetate iron (II) propionate, ammonium acetate and ammonium butyrate, and "solid" acids such as bentonites, zeolites or montmorillonites, which may be additionally activated with mineral acids, also acid ion exchangers. These acid catalysts may be used in the usual quantities.

Organic proton acids for example can be used in an amount from 0.01 Mol-% to 10 Mol-% based on the amount of starting compound of formula (II).

The process according to the invention can also be carried out using inert solvents and/or diluents, for example benzene, toluene, xylene, halogenated benzenes, nitrobenzene, cyclohexane, cyclohexanone, methylene chloride, chloroform or carbon tetrachloride. These solvents may be employed in the usual quantities.

The bisphenols of formula I may be reacted by known methods (Houben-Weyl, Methoden der organischen Chemie, Vol. VIII, 1952, pages 101 to 104, or R. E. Oesper et al. J. Am. Chem. Soc. 47, 2609 (1925)) to form the corresponding bis-chlorocarbonic acid esters corresponding to the formula (IV):

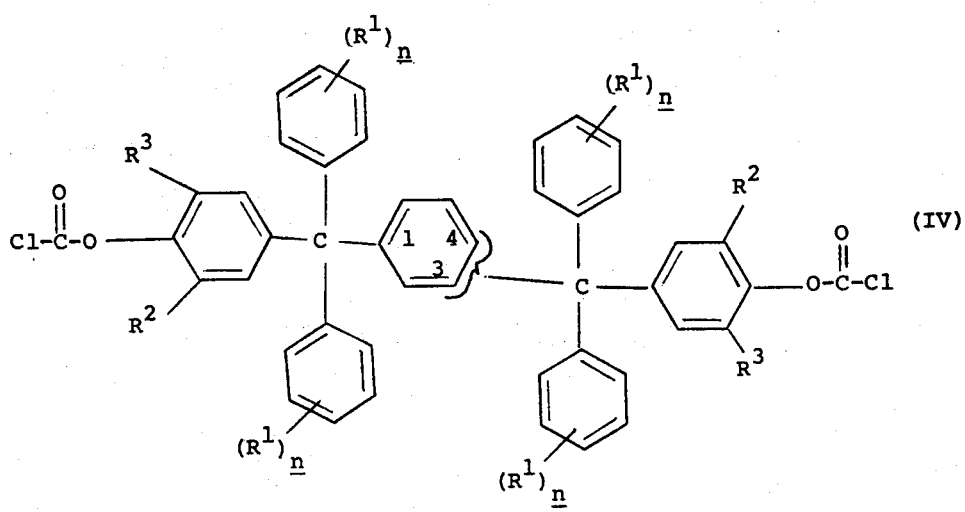

in which $R^1$, $R^2$, $R^3$ and $n$ are as defined in reference to formula I.

In general, the bis-chlorocarbonic acid esters of formula IV are produced by dissolving or suspending α,αλ ,α', α'-tetrakisaryl-α,α'-bis-(4-hydroxyphenyl)-1,3- or 1,4-dimethyl benzenes in an inert organic solvent, for example benzene, toluene, xylene, chlorobenzene, dichlorobenzene, methylene chloride, chloroform or carbon tetrachloride, and reacting the resulting solution or suspension with 2 to 10 times the molar quantity of phosgene in the presence of twice to three times the molar quantity of a tertiary base, for example N, N-diemthyl aniline, pyridine or alkylated pyridines, which are intended to bind the hydrogen chloride gas evolved during the reaction, at temperatures in the range from 0 to 200°C. and preferably at temperatures in the range from 20 to 150°C.

However, it is also possible initially to introduce a solution of phosgene in an inert organic solvent, followed by the dropwise addition at temperatures of from 0 to 50°C of a solution or suspension of the bisphenol of general formula I and the tertiary base in an inert organic solvent. In order to complete the reaction, the temperature is increased, optionally slowly, up to the boiling temperature of the solvent used.

On completion of the reaction, excess phosgene, if any, is removed from the reduction mixture either by passing through an inert gas stream, for example nitrogen, or with greater advantage by distillation together with some of the solvent used. The hydrochloric acid amine salts formed as secondary products are subsequently washed out by repeated extraction of the organic solution with water. Concentration of the dried organic phase by evaporation leaves the bis-chlorocarbonic acid esters generally in the form of solid residues which may be purified by conventional techniques, for example by precipitation, crystallization or by dissolution and crystallization or recrystallization. The bis-chlorocarbonic acid esters of the following compounds for example maybe produced in this way:

$\alpha, \alpha, \alpha', \alpha'$-tetraphenyl-$\alpha,\alpha'$-bis-(4-hydroxyphenyl)-1,4-dimethyl benzene;

$\alpha, \alpha, \alpha', \alpha'$-tetraphenyl-$\alpha,\alpha'$-bis-(4-hydroxyphenyl)-1,3-dimethyl benzene;

$\alpha,\alpha,\alpha', \alpha'$-tetrakis-(4-fluorophenyl)-$\alpha,\alpha'$-bis-(4-hydroxyphenyl)1,4-dimethyl benzene;

$\alpha, \alpha, \alpha', \alpha'$-tetrakis-(4-chlorophenyl)-$\alpha,\alpha'$-bis-(4-hydroxyphenyl)1,4-dimethyl benzene;

$\alpha, \alpha, \alpha', \alpha'$-tetrakis-(3,4-dichlorophenyl)-$\alpha,\alpha'$-bis-(4-hydroxyphenyl)-1,4-dimethyl benzene;

$\alpha, \alpha, \alpha', \alpha'$-tetraphenyl-$\alpha,\alpha'$-bis-(4-hydroxy-3,5-dimethylphenyl)1,4-dimethyl benzene; and $\alpha,\alpha,\alpha',\alpha'$-tetraphenyl-$\alpha,\alpha'$-bis-(4-hydroxy-3-chlorophenyl)-1.4-dimethyl-benzene.

The compounds of formula I are valuable intermediate products, for example for the production of high molecular weight aromatic polycarbonates. These polycarbonates are obtained by conventional methods from the bisphenols of formula I or from the corresponding bis-chlorocarbonic acid esters of formula IV, and are distinguished by extremely high solidification points and dimensional stability under heat, and may be used for example in the manufacture of high-temperature-resistant electrical insulating films.

Further details of these new aromatic polycarbonates may be found in German Patent Application No. P24 25 291 filed on the same date and the U.S. application Ser. No. 579,532, filed 5/1/75 by the same inventors entitled HIGH MOLECULAR WEIGHT POLYCARBONATES OF $\alpha, \alpha, \alpha, \alpha', \alpha', \alpha'$-HEXAKISARYL-1,3- AND/OR -1,4-DIMETHYL BENZENES

EXAMPLE 1

110 g of $\alpha, \alpha, \alpha', \alpha'$-tetraphenyl-$\alpha, \alpha'$-dihydroxy-1,4-dimethyl benzene (0.25 mol) were heated to reflux in a water separator together with 300 g of phenol (3.2 mols) and 200 ml of toluene. 8 to 9 ml of water separated after some 4 hours. The toluene was then distilled off under normal pressure and the residue digested at room temperature with 500 ml of methylene chloride, filtered under suction and the solids were extracted by boiling with 300 ml of methylene chloride. After further filtration under suction, the product was recrystallized from cyclohexanone. The combined mother liquors were concentrated and the phenol was distilled off, followed by working up with more methylene chloride.

Total yield: 136 g of $\alpha, \alpha, \alpha', \alpha'$-tetraphenyl-$\alpha,\alpha'$-bis-(4hydroxyphenyl)-1,4-dimethyl benzene (91% of the theoretical yield).

Mp.: 314°C, $C_{44}H_{34}O_2$ (594.8)

Calculated: C 88.86 H 5.76 0 5.38 phenol OH 5.72%
Found: C 98.6 H 5.98 0 5.42 phenol OH 5.6%

EXAMPLE 2

110 g of $\alpha, \alpha, \alpha', \alpha'$-tetraphenyl-$\alpha,\alpha'$-dihydroxy-1,4-dimethyl benzene (0.25 mol) were slowly heated to 130°C together with 600 g of phenol (6.5 mols). After 3 hours at 130°C, the temperature was increased and approximately 300 g of phenol were distilled off under normal pressure. The reaction mixture was left to cool, followed by working up as described in Example 1. Yield: 124 g of $\alpha, \alpha, \alpha', \alpha'$-tetraphenyl-$\alpha,\alpha'$-bis-(4-hydroxyphenyl)-1,4-dimethyl benzene (85% of the theoretical yield); m.p. 312° – 316°C.

EXAMPLE 3

120 g of $\alpha, \alpha, \alpha', \alpha'$-tetraphenyl-$\alpha,\alpha'$-dichloro-1,4dimethyl benzene (0.25 mol) were slowly heated to 90°C together with 300 of phenol, and the temperature was increased to 130°C after 2 hours at 90°C. After another 2 hours at 130°C, the reaction mixture was worked up in the same way as in Example 1. Yield: 132 g of $\alpha, \alpha, \alpha', \alpha'$-tetraphenyl-$\alpha,\alpha'$-bis-(4-hydroxyphenyl)-1,4-dimethyl benzene (89% of the theoretical yield); m.p.: 316° – 320°C.

EXAMPLE 4

Hydrogen chloride gas was introduced at 55°C up to saturation point into a mixture of 110 g (0.25 mol) of $\alpha, \alpha, \alpha', \alpha'$-tetraphenyl-$\alpha,\alpha'$-dihydroxy-1,4-dimethyl benzene and 350 g of phenol (3.7 mols). The reaction mixture was then heated to 90°C, followed by stirring for 2 hours at 90°C. The temperature was then increased to 130°C, as a result of which hydrochloric acid distilled off. After 3 hours at 130°C, the reaction mixture was left to cool, followed by working up in the same way as in Example 1.

Yield: 138 g (93% of the theoretical yield) of $\alpha, \alpha, \alpha', \alpha'$tetraphenyl-$\alpha,\alpha'$-bis-(4-hydroxy-phenyl)-1,4-dimethyl benzene; m.p.: 310° – 312°C.

EXAMPLE 5

26 g of $AlCl_3$ (0.2 mol) were suspended in 100 ml of benzene, followed by the dropwise addition under reflux of a solution of 31 g of $\alpha, \alpha, \alpha, \alpha', \alpha', \alpha'$-hexachloro-p-xylene (0.1 mol) in 50 ml of benzene). After 1 hour under reflux, the mixture was cooled to 50°C, 140 g of phenol (1.5 mol) were added and the mixture was slowly heated to reflux. When the evolution of hydrogen chloride ceased, the temperature was increased to 130°C and benzene distilled off under normal pressure. The temperature was adjusted to 160°C and, after 1 hour, the reaction product worked up in the same way as in Example 1.

Yield: 33 g (56% of the theoretical yield) of $\alpha, \alpha, \alpha', \alpha'$-tetraphenyl-$\alpha,\alpha'$-bis-(4-hydroxyphenyl)-1,4- dimethyl benzene; m.p.: 308° – 310°C.

EXAMPLES 6 TO 10

The compounds mentioned in the following list were produced by the method used in Examples 1, 3 and 4, taking into account the corresponding molar ratios. Elemental analyses of all the compounds mentioned were conducted in order to determine their carbon, hydrogen, oxygen and halogen contents, all of which were found to be satisfactorily consistent with the calculated values.

EXAMPLE 6

Phenol and $\alpha, \alpha, \alpha', \alpha'$-tetraphenyl-$\alpha,\alpha'$-dihydroxy1,3-dimethyl benzene were reacted in a 12.8 : 1 mol ratio to produce $\alpha, \alpha, \alpha', \alpha'$-tetraphenyl-$\alpha,\alpha'$-bis-(4-hydroxyphenyl)1,3-dimethyl benzene, in accordance with Example 1

Yields: 82% mp.: 258°–262°C. Phenol and $\alpha.\alpha.\alpha'.\alpha'$-Tetraphenyl$\alpha.\alpha'$-dichlor-1.3-dimethylbenzene were reacted in a 12.81:1 mol ratio to produce $\alpha.\alpha.\alpha'.\alpha'$-tetraphenyl-$\alpha.\alpha'$-bis-(4-hydroxyphenyl)1.3-dimethylbenzene in accordance with Example 3: Yield: 86 %, m.p.: 260°–264°C.

EXAMPLE 7

Phenol and $\alpha, \alpha, \alpha', \alpha'$-tetrakis-(p-fluorophenyl)$\alpha,\alpha'$-dichloro-p-xylene were reacted in a 12.8 : 1 mol ratio to produce $\alpha, \alpha, \alpha', \alpha'$, -tetrakis-(p-fluorophenyl)-$\alpha,\alpha'$-bis-(4-hydroxyphenyl)-1,4-dimethyl benzene (m.p.: 301 °–303°C, Yield 78%) in accordance with Example 3.

EXAMPLE 8

Phenol and $\alpha, \alpha, \alpha', \alpha'$-tetrakis-(p-chlorophenyl)$\alpha,\alpha'$-dihydroxy-1,4-dimethylbenzene were reacted at a mol ratio of 12.8 : 1 to produce $\alpha, \alpha, \alpha', \alpha'$-tetrakis-(p-chlorophenyl)-$\alpha,\alpha'$bis-(4-hydroxyphenyl)-1,4-dimethyl benzene (m.p.: 316° – 318°C, Yield: 81%) in accordance with Example 1.

Example 9

Phenol and $\alpha,\alpha, \alpha', \alpha'$-tetrakis-(3,4-dichlorophenyl)$\alpha,\alpha'$-dichloro-1,4-dimethyl benzene were reacted at a mol ratio of 12.8 : 1 to produce $\alpha, \alpha, \alpha', \alpha'$, -tetrakis-(3,4-dichlorophenyl)$\alpha,\alpha'$-bis-(4-hydroxyphenyl)-1,4-dimethyl benzene (m.p.: 274°C, Yield: 73%) in accordance with Example 3.

EXAMPLE 10 o,o'-dimethyl phenol and $\alpha, \alpha, \alpha', \alpha'$-tetraphenyl$\alpha,\alpha'$-dihydroxy-1,4-dimethyl benzene were reacted at a mol ratio of 14.8 : 1 to produce $\alpha, \alpha, \alpha', \alpha'$-tetraphenyl-$\alpha,\alpha'$-bis-(4hydroxy-3,5-dimethylphenyl)-1,4-dimethyl benzene (m.p.: 280° – 284°C, Yield: 54%) in accordance with Example 4.

EXAMPLE 11

$\alpha, \alpha, \alpha', \alpha'$-Tetraphenyl-$\alpha,\alpha'$-bis-(4-chloroformyl hydroxy phenyl)-1,4-dimethyl benzene (method A)

47.6 g (0.08 mol) of $\alpha, \alpha, \alpha', \alpha'$-tetraphenyl-$\alpha,\alpha'$-bis-(4-hydroxyphenyl)-1,4-dimethyl benzene and 21.4 g (0.176 mol) of N,N-dimethyl aniline, were introduced into 750 ml of anhydrous toluene. 63.3 g (0.64 mol) of phosgene were introduced into the thoroughly stirred suspension over a period of 90 minutes at approximately 90 to 95°C, as a result of which the dihydroxy compound reacted to form the bis-chlorocarbonic acid ester and entered into solution. In order to complete the reaction, the reaction mixture was stirred for 1 hour at 90°C, after which excess phosgene was removed by introducing dry nitrogen. After cooling to room temperature, the amine hydrochloride precipitated was filtered off, the organic phase was washed twice with 1 N hydrochloric acid and then with water until free from chloride, dried over $Na_2SO_4$, concentrated by evaporation to dryness and, finally, dried for 12 hours at 80°C/15 Torr. Crude Yield: 54.7 g (95% of the theoretical yield) of a light brown product melting at 245° to 249°C. Recrystallization from xylene gives 38.6 g (67% of the theoretical) of pale yellowish crystals melting at 251° – 252°C. Cl-analysis: Calculated 9.85%, Found 9.7%.

When the same reaction is carried out at 70°C and 110°C (reflux), 88% and 92%, respectively, of crude bis-chlorocarbonic acid ester are obtained. At reaction temperatures below 70°C, some of the $\alpha, \alpha, \alpha', \alpha'$-tetraphenyl-$\alpha,\alpha'$-bis-(4-hydroxyphenyl)-1,4-dimethyl benzene is left behind unreacted under the aforementioned conditions (for example 40 to 45% at 50°C.).

The bis-chlorocarbonic acid esters mentioned in Table 1 were produced under the conditions described in Example 11 for the production of $\alpha, \alpha, \alpha', \alpha'$-tetraphenyl-$\alpha,\alpha'$-bis-(4-chloroformyl hydroxyl phenyl)-1,4-dimethyl benzene, in some instances with certain minor modifications.

EXAMPLE 12

$\alpha, \alpha, \alpha', \alpha'$-Tetraphenyl-$\alpha,\alpha'$-bis-(4-chloroformyl hydroxy phenyl)-1,4-dimethyl benzene (method B)

99 g (1 mol) of $COCl_2$ were condensed at −5° to −15°C in 600 ml of anhydrous toluene. A suspension of 149 g (0.25 mol) of $\alpha, \alpha, \alpha', \alpha'$-tetraphenyl-$\alpha,\alpha'$-bis-(4-hydroxyphenyl)-1,4-dimethyl benzene in a mixture of 66.6 g (0.55 mol) of N,N-dimethyl aniline and 1400 ml of anhydrous toluene, was run into this solution with stirring over a period of 15 minutes at a temperature of 10° to 20°C. The reaction mixture was then heated from 20°C to 90°C over a period of 3 hours, and stirred for another 2 hours at 90°C. 500 ml of toluene were then distilled off from the blue-green suspension formed while nitrogen was passed through it, excess phosgene distilling off with the toluene. After the reaction mixture had been cooled, undissolved fractions [amine hydrochloride and unreacted bisphenol (15% of the quantity used)] were filtered off and the organic phase was worked up in the same way as in Example 11. Crude yield 122 g (67.8% of the theoretical yield), m.p.: 238° – 245 °C.

Table 1

α, α, α', α'-Tetrabisaryl-α,α'-bis-(4-chloroformyl hydroxy phenyl)-dimethyl benzenes[a]

| Compound | Reaction temperature [°C] | Crude yield [% of theoretical] | Mp:[b] [°C] | Cl-analysis Calculated | Cl-analysis Found |
|---|---|---|---|---|---|
| α,α,α',α'-tetraphenyl-α,α'-bis-(4-chloroformyl hydroxyphenyl)-1,4-dimethyl benzene | 90–95 | 95 | 251–252 | 9.85 | 9.7 |
| α,α,α',α'-tetraphenyl-α,α'-bis-(4-chloroformyl hydroxyphenyl)-1,3-dimethyl benzene | 70 | 94 | 106–110 | 9.85 | 9.6 |
| α,α,α',α'-tetrakis-(4-fluorophenyl)-α,α'-bis-(4-chloroformyl hydroxyphenyl)-1,4-dimethyl benzene | 70 | 89 | 234–236 | 8.98 | 8.9 |
| α,α,α',α'-tetrakis-(4-chlorophenyl)-α,α'-bis-(4-chloroformyl hydroxyphenyl)-1,4-dimethyl benzene | 55–60 | 91 | 231–233 | 24.8 | 24.3 |
| α,α,α',α'-tetrakis-(3,4-dichlorophenyl)-α,α'-bis-(4-chloroformyl hydroxyphenyl)-1,4-dimethyl benzene | 75 | 98 | 288–290 | 35.6 | 34.4 |
| α,α,α',α'-tetraphenyl-α,α'-bis-(4-chloroformyl hydroxy-3,5-dimethylphenyl)-1,4-dimethyl benzene | 70 | 95 | 225–230 | 9.15 | 8.95 |

[a]prepared by method A (cf. Example 11)
[b]after recrystallization

PRODUCTION OF A POLYCARBONATE

A solution of 7.1 g (0.01 mol) of α,α, α', α'-tetraphenyl-α,α'-bis-(p-chloroformyl hydroxyphenyl)-1,4-dimethyl benzene in 60 ml of $CH_2Cl_2$ was run quickly with intensive stirring at 20° to 25°C into an aqueous solution of 1.8 g (0.045 mol) of NaOH in 45 ml of water, followed by the addition of 3 ml of a 1% aqueous triethylamine solution. The reaction mixture was then stirred for 1 hour. The entire reaction was carried out in an atmosphere of nitrogen. The aqueous phase was separated off, the organic phase diluted with 100 ml of $CHCl_3$ and washed twice with 100 ml of 2% $H_3PO_4$ and, finally, with distilled water until neutral. After drying over anhydrous $Na_2SO_4$, the organic phase was concentrated to a residual volume of approximately 50 ml and added dropwise to $CH_3OH$, the polycarbonate being precipitated in the form of white flakes. Drying for 15 hours at 100°C/15 Torr left 5.9 g (95%) of polycarbonate. $\eta_{rel}$ = 1.234 ($CHCl_3$); $M_{LS}$ =114 000 Second order transition point (as determined by differential thermoanalysis = DTA): 228°C For standard commercial-grade polycarbonate of 2,2-bis-(4-hydroxyphenyl)-propane (bisphenol A): 150°C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of α,α,α,α',α',α'-hexakisaryl-1,3- and -1,4-dimethyl benzenes corresponding to the formula

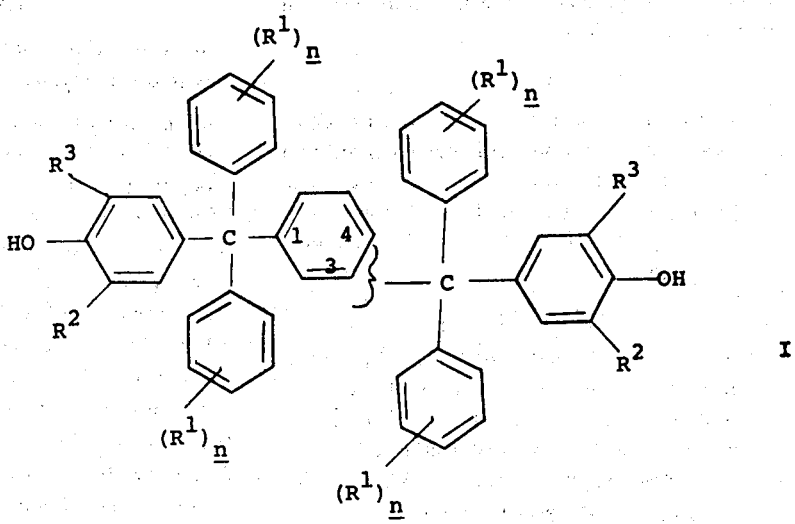

I in which
R¹ represents C₁-C₄ alkyl, halogen or H,
n = 1, 2 or 3, and
R² and R³ independently of one another represent C₁-C₃ alkyl, halogen or H,
wherein α,α,α',α'-tetrakisaryl-1,3- or 1,4-bis-(chloromethyl) or -bis-(hydroxymethyl)-benzenes corresponding to the formula

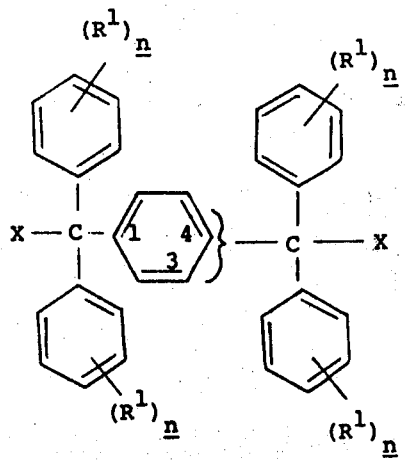

II in which X represents chlorine or OH, while R¹ and n are defined as in formula I, are reacted with about 2 to 30 times the molar quantity of a phenol corresponding to the formula

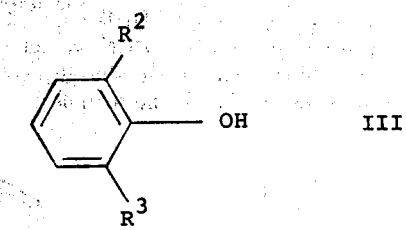

III in which R² and R³ are defined as in formula I, at temperatures in the range from about 30°C to 300°C.

2. The process of claim 1 wherein the phenol of formula III is present at about 6 to 15 times the molar quantity of the compounds of formula II and the reaction temperature is between about 60 to 200°C.

3. The process of claim 1 wherein R¹ is H, CH₃, F, Cl or Br and R² and R³ are both H.

4. A process for the production of α, α, α, α', α', α'-hexakisaryl-1,3- and -1,4-dimethyl benzenes corresponding to the formula

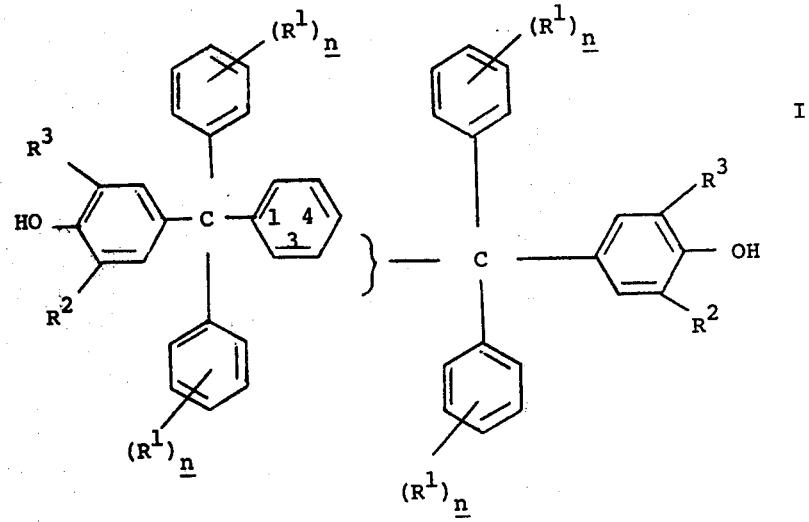

I in which
R¹ represents C₁-C₄ alkyl, halogen or H,
n = 1, 2 or 3 and
R² and R³ independently of one another represent C₁-C₃ alkyl, halogen, or H,
comprising reacting α, α, α', α'-tetrakisaryl-1,3- or -1,4-bis(chloromethyl) or -bis-(hydroxymethyl)-benzenes corresponding to the formula

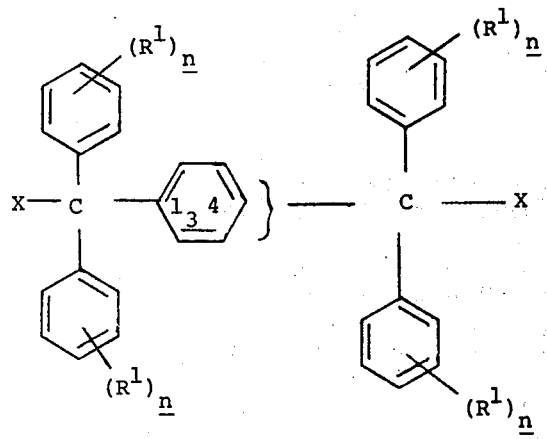

in which X represents chlorine or OH, while R¹ and n are defined as in formula I, with about 2 to 30 times the molar quantity of a phenol corresponding to the formula

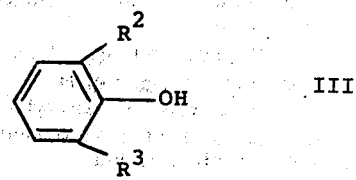

in which R² and R³ are defined as in formula I, at temperatures in the range from about 30°C to 300°C.

* * * * *